(12) United States Patent
Duckert et al.

(10) Patent No.: US 8,489,182 B2
(45) Date of Patent: Jul. 16, 2013

(54) SYSTEM AND METHOD OF QUALITY ANALYSIS IN ACQUISITION OF AMBULATORY ELECTROCARDIOGRAPHY DEVICE DATA

(75) Inventors: David W. Duckert, Wauwatosa, WI (US); Patrick J. Dorsey, Wauwatosa, WI (US)

(73) Assignee: General Electric Company, Schenectady, NY (US)

( * ) Notice: Subject to any disclaimer, the term of this patent is extended or adjusted under 35 U.S.C. 154(b) by 51 days.

(21) Appl. No.: 13/276,045

(22) Filed: Oct. 18, 2011

(65) Prior Publication Data

US 2013/0096450 A1  Apr. 18, 2013

(51) Int. Cl.
*A61B 5/00* (2006.01)

(52) U.S. Cl.
USPC ........................................................ 600/509

(58) Field of Classification Search
USPC .................................. 600/508–525, 300, 301
See application file for complete search history.

(56) References Cited

U.S. PATENT DOCUMENTS

| | | | |
|---|---|---|---|
| 7,072,709 B2 | 7/2006 | Xue | |
| 2006/0293273 A1 | 12/2006 | Mangano | |
| 2007/0202515 A1 | 8/2007 | Hadlock et al. | |
| 2008/0065468 A1 | 3/2008 | Berg et al. | |
| 2009/0171227 A1 | 7/2009 | Dziubinski et al. | |
| 2009/0270694 A1 | 10/2009 | Hyde et al. | |
| 2010/0030089 A1 | 2/2010 | Hyde et al. | |
| 2010/0041964 A1 | 2/2010 | Hyde et al. | |
| 2010/0174586 A1 | 7/2010 | Berg et al. | |
| 2010/0240982 A1 | 9/2010 | Westbrook et al. | |
| 2010/0249623 A1 | 9/2010 | Makdissi | |
| 2010/0256699 A1 | 10/2010 | Makdissi | |

OTHER PUBLICATIONS

Seer 12 GE Healthcare. http://www.gehealthcare.com/euen/cardiology/docs/SEER_12_spec_e.pdf, 2010.
MARS Ambulatory ECG Analysis. http://www.gehealthcare.com/euen/cardiology/docs/MARS_Algorithms_bro_e.pdf, 2010.
MARS Enterprise, Ambulatory ECG System. http://www.gehealthcare.com/euen/cardiology/docs/MARS_Enterprise_spec_e.pdf, 2010.
MARS Holter Analysis System. http://www.gehealthcare.com/euen/cardiology/products/diagnostic_ecg/holter/mars_pc/index.html, observed on Oct. 18, 2011.
CARESCAPE Clinical Information Center. http://www.gehealthcare.com/euen/patient_monitoring/docs/CIC-Pro_bro_M1120510_eng.pdf, 2008.
MUSE Cardiology Information System. https://www2.gehealthcare.com/portal/site/usen/ProductLineDetail? vgnextoid= 6a309daa2d930210VgnVCM1000 0024dd1403RCRD, 2007.
"Galix WinTer Holter Analyszer" User's Manual, Galix Biomedical Instrumentation, Inc. as observed on Oct. 18, 2011.

*Primary Examiner* — Scott Getzow
(74) *Attorney, Agent, or Firm* — William Kryger

(57) ABSTRACT

A quality control system in combination with an ECG data analysis system to analyze ECG data acquired by an ambulatory electrocardiography device via a cable having a plurality of leads connected to a subject is provided. The quality control system includes a memory having programmable instructions for execution by a processor to perform the steps of calculating a trend of a quality score in the ECG data dependent on a noise content in the ECG data; and calculating a probability that one of a hardware and the Hookup personal, each associated with collecting the ECG data from the subject, is a substantial cause of the quality score for the ECG data. The probability can be calculated based on a comparison the trend of the quality score associated with the Hookup personnel versus the trend of the quality score of the hardware employed in acquiring the ECG data.

19 Claims, 4 Drawing Sheets

SYSTEM AND METHOD OF QUALITY ANALYSIS IN ACQUISITION OF AMBULATORY ELECTROCARDIOGRAPHY DEVICE DATA

FIELD OF USE

The subject matter generally relates to a system and method of analysis of noise content in an acquired electrocardiogram (ECG) by an ECG data analysis system.

BACKGROUND

An ambulatory electrocardiography device (including a "Holter" or "Holter recorder" or monitor) is a device known in the portable acquisition of electrocardiograms (ECGs). The ECG data can later be downloaded from the device to an ECG data analysis system for analysis to identify cardiac arrhythmias or other cardiac abnormalities. Poor preparation of the patient or improper placement of the device leads to the patient can result in excessive noise content, and consequent low quality ECG data. Needless to say, ECG data having excessive noise content can be more expensive, difficult and time consuming to analyze.

In use of the above-described ambulatory electrocardiography device, one drawback is that often the hookup personnel or hookup placement technician or hookup tech that connects the ambulatory electrocardiography device to the subject or patient may not be the same as the user that analyzes the data. As a result, the hookup personnel that prepares the patient and places the device leads does not readily know whether poor placement led to poor quality ECG data for analysis.

BRIEF SUMMARY

There is a need and desire for a quality control system and method that provides feedback to the hookup personnel responsible so as to improve the preparation of the patient and placement of the device leads to acquire ECG data from the patient. The system should automate the method such that the feedback is provided in a consistent and timely manner. The above-mentioned drawbacks and needs are addressed by the embodiments described herein in the following description.

According to one embodiment of the subject matter described herein, a quality control system in combination with an ECG data analysis system to analyze ECG data acquired by an ambulatory electrocardiography device via a cable having a plurality of leads connected to a subject is provided. The quality control system includes a memory or non-transitory medium having programmable instructions for execution by a processor to perform the steps of calculating a trend of a quality score in the ECG data dependent on a noise content in the ECG data; and calculating a probability that one of a hardware and the hookup personnel, each associated with collecting the ECG data from the subject, is a substantial cause of the quality score for the ECG data. The probability can be calculated based on a comparison the trend of the quality score associated with the hookup personnel versus the trend of the quality score of the hardware employed in acquiring the ECG data.

According to another embodiment of the subject matter described herein, a quality control system in combination with an ECG data analysis system to analyze ECG data acquired by an ambulatory electrocardiography device via a cable having a plurality of leads connected to a subject is provided. The improvement includes the quality control system creates a display of a probability that a unique hookup personnel versus a hardware is a source of noise detected in an acquired ECG data of the subject.

Systems and methods of varying scope are described herein. In addition to the embodiments described in this summary, further embodiment may become apparent by reference to the drawings and with reference to the detailed description that follows.

DETAILED DESCRIPTION

In the following detailed description, reference is made to the accompanying drawings that form a part hereof, and in which is shown by way of illustration specific embodiments, which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

Figure 1:
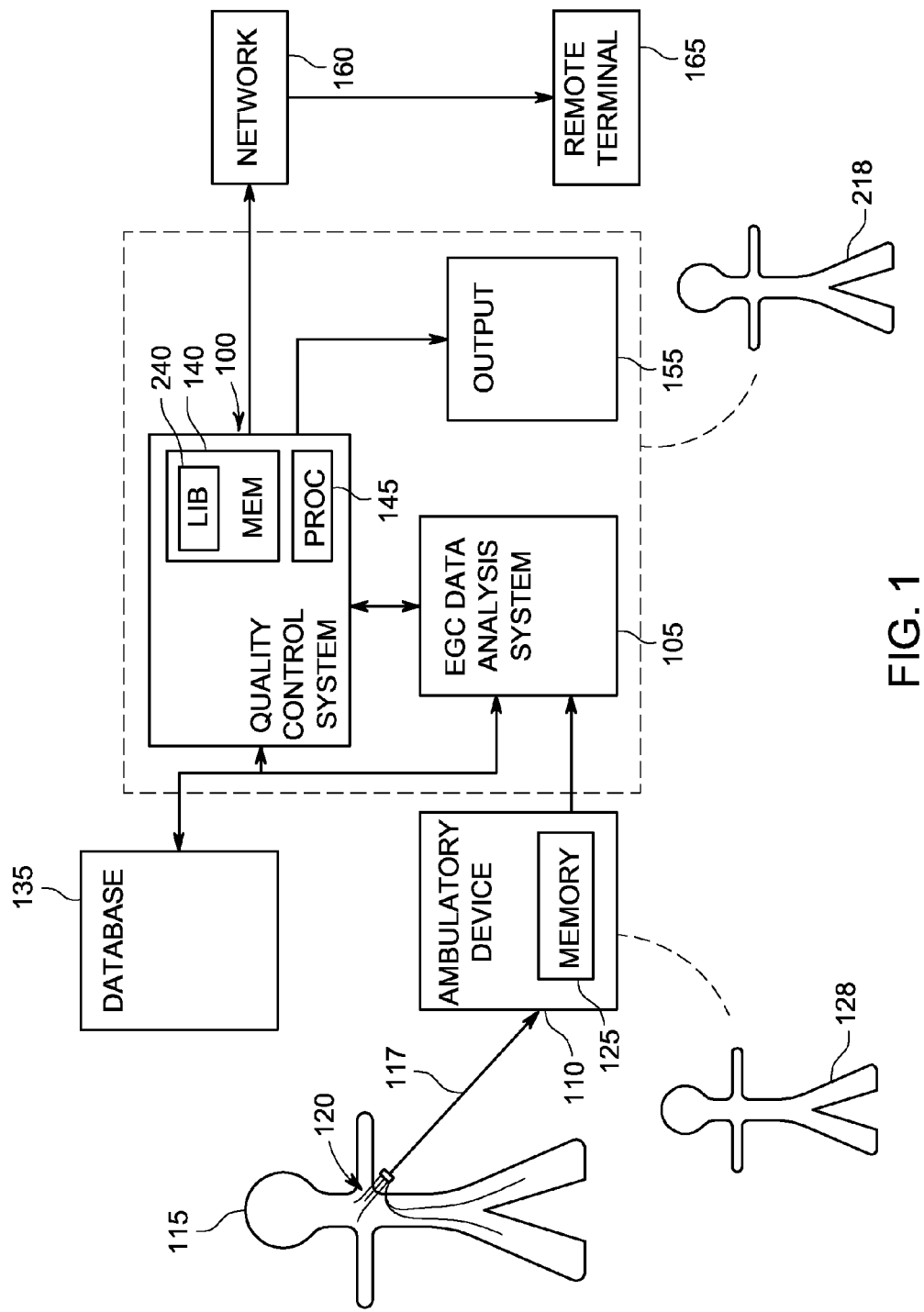
FIG. 1 shows a schematic diagram of an embodiment of a system that can be employed in combination with an ECG data analysis system in accordance to the subject matter described herein.

FIG. 1 illustrates an embodiment of a quality control system 100 of the subject matter described herein employed in combination with an ECG data analysis system 105 analyzing electrocardiogram ECG data acquired with an ambulatory electrocardiography device 110 placed on a subject 115.

The ambulatory electrocardiography device 110 can include or be a Holter recorder or monitor or similar functioning device having a cable 117 with multiple leads 120 placed in a known manner on the subject 115 to acquire the ECG data. Typically, the ambulatory electrocardiography device 110 is configured to be portable in the acquisition of the ECG data from the subject 115 over a defined time period (e.g., 24 hours, 48 hours, 72 hours, etc.). An example embodiment of the ambulatory electrocardiography device 110 can be a SEER 12 digital recorder as manufactured by GE Healthcare, a division of the General Electric Company. The ambulatory electrocardiography device 110 can include a memory or computer readable storage medium 125 operable to store the acquired ECG data, as well as the subject's demographic data and hookup personnel 128 identification, for later download to a database 135 or directly to the ECG data analysis system 105. The ambulatory electrocardiography device 110 can also include pacemaker detection.

The ECG data analysis system 105 can be generally configured to receive the ECG data from the ambulatory electrocardiography device 110 for analysis and illustration. One exemplary embodiment of the ECG data analysis system 105 can be a MARS ECG data analysis system as manufactured by GE Healthcare, a division of the General Electric Company that is operable to mark or flag (but not quantify) a location of ECG data automatically identified by the ECG data analysis system to substantially include noise. The ECG data analysis system 105 can include a suite of diagnostic tools (e.g., QT interval measurement, atrial fibrillation detection, etc.) to analyze the ECG data received from the ambulatory electrocardiography device 110. The ECG data analysis system 105 can be configured to also store the received ECG data for ready access. In addition to receiving ECG data from the ambulatory electrocardiography device 110, the ECG data analysis system 105 can also be configured to receive the ECG from various sources (e.g., cardiology information system (CIS) storing legacy ECG data at the database 135).

The quality control system 100 of the subject matter described herein can independent of or integrated with the ECG data analysis system 105 (as shown in dashed line). The quality control system 100 can generally include a memory 140 (e.g., computer readable or non-transitory medium such as a hard drive, CD, DVD, flash drive, etc.) operable to store program instructions for execution by a processor 145.

The quality control system 100 can also include an input 150 and an output 155. The input 150 can include a computer interface with a touchscreen, mouse, keyboard, etc. independent of or integrated with the ECG data analysis system. The output 155 can include a display monitor, LEDs, speaker, printer, etc. that can be independent of or integrated with the ECG data analysis system 105. The quality control system 100 can also be in communication via a network (e.g., intranet, LAN, WAN, VPN or the Internet, etc.) 160 to a remote terminal 165.

Figure 2:
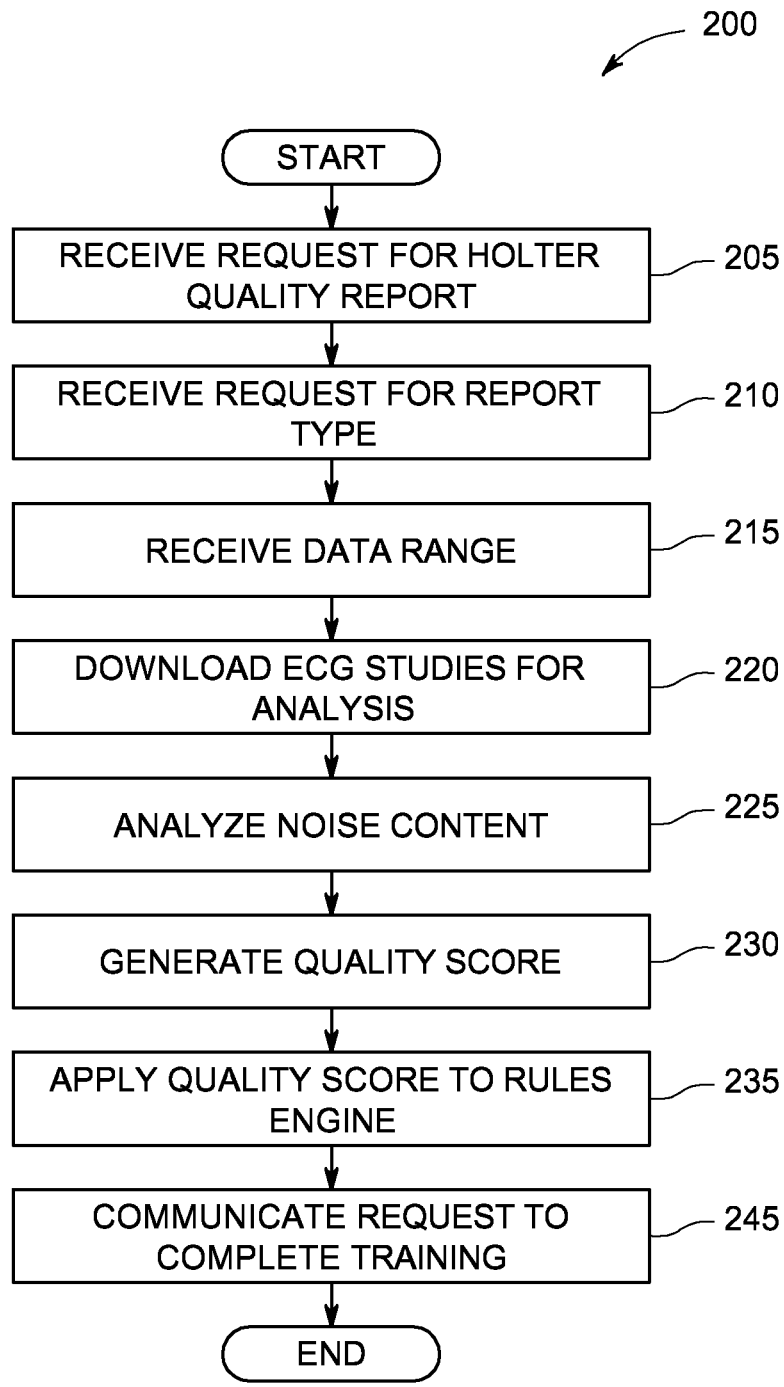
FIG. 2 shows a schematic diagram of an embodiment of a method of operating the system of FIG. 1 in accordance to the subject matter described herein.

Having generally provided the above-description of a construction of the embodiment the quality control system 100 of the subject matter described herein in combination with the ECG data analysis system 105 and ambulatory electrocardiography device 110, the following is a general description of a method 200 of operation of the quality control system 100 as shown in FIG. 2. It should be understood that the sequence or succession of the acts or steps of the method 200 as described in the foregoing description can vary. Also, it should be understood that the method 200 may not require each act or step in the foregoing description, or may include additional acts or steps not disclosed herein. One or more of following steps and acts of the method 200 can also be in the form of computer-readable program instructions stored on the computer readable or non-transitory medium or memory (e.g., hard drive of a computer, CD, DVD, flash drive, etc.) 140 for execution by the processor 145 of a computer programmable device or independent thereof.

Assume at the start of the method 200 that the quality control system 100 includes the memory 140 that stores a plurality of training modules to educate the Hookup technician on various techniques or protocol to properly place device leads 120 on the subject 115 so as to obtain quality ECG data. Each of the training modules can be associated with the quality score for the placement of the device leads 120 as generated and output from the quality control system 100.

The method 200 can include step 205 of receiving a request for a quality report. Step 210 can include communicating a prompt and receiving a request for a type of quality report (e.g., quality of acquired ECG data versus a hookup personnel 128 or hardware (e.g., ambulatory electrocardiography device 110, cable 117, leads 120) employed in acquisition of the ECG data)). It should be understood that the hookup personnel or hookup placement technician or hookup tech 128 can be a trained professional or the subject 115 or another individual that placed the leads for acquisition of the ECG data from the subject 115.

Step 215 can include receiving data from a user 218 of the quality control system 100 (the user 218 distinguished and independent of the hookup personnel 128) directed to an identification of the hookup personnel 128 of interest for the quality report, an ambulatory electrocardiography device 110 identification or serial number, a device cable 117 (i.e., bundle of leads to a common connector leading to the ambulatory electrocardiography device) serial number, a device lead 120 identifier, a date of device ECG data acquisition being analyzed, an identification number for the ECG data set (e.g., case study identification number) being analyzed, an identification of the clinic where the device acquired ECG data was acquired. The input data received at the quality control system 100 can further define the limits of the analysis for the quality report, including a time period or range of dates of interest for the ECG data for analysis by the quality control system 100 in combination with the ECG data analysis system 105, a measure of minutes of noise before the device ECG data to be analyzed, a measure of the minutes of noise after the device ECG data to be analyzed, a measure of time of duration of device ECG data to be analyzed (can be from one or more placements of device leads for a particular hookup personnel 128), a number of device ECG data acquisitions performed by particular hookup personnel 128, etc.

Step 220 can include downloading or retrieving the ECG data for analysis. It is assumed for sake of example that the ECG data can be received from the ambulatory electrocardiography device 110, or from a computer readable storage medium containing the ECG data from the ambulatory electrocardiography device 110 or the database 135. For example, the ECG data can be received from the database 135 based on the received range of dates of interest in Step 215.

Step 225 can include conducting signal analysis to calculate a noise content of the ECG data. One embodiment of the ECG data analysis system 105 can calculate a percentage of noise content in the acquired ECG data based on predetermined thresholds programmed (e.g., pass through high or low band pass filters that removes data to be ignored) into the ECG data analysis system 105. After passing through the band pass filters, a substantially flat ECG waveform (almost all ECG data ignored) can be equated to a threshold percent (e.g., one hundred percent) noise content in the ECG data. The quality control system 100 can calculate and mark the region of the ECG data (e.g., time period) that consists substantially of noise content. The quality control system 100 can then measure the noise content of the ECG data based on a total time period (e.g., minutes or hours of noise) of acquired ECG data analyzed to be substantially noise content (e.g., almost all ECG data ignored). The quality control system 100 can also receive instructions from the user 218 (e.g., ECG analysis technician or user) that designates or marks the regions in the acquired time period of ECG data to be ignored as substantially noise content, independent of or supplement to automatic calculation of noise content described above. Per the instructions from the user 218, the quality control system 100 can designate or modify automatically calculated regions of noise content such that that all the ECG data in the designated region per the user's instructions can be ignored as substantially noise content.

Step 230 can include generating a quality score for one or more hookup personnel or placement technicians 128 associated with the ECG data for analysis. Step 230 can include generating a prompt at the output 155 to request a subjective placement score to be assigned by a user 218 (e.g., clinician analyzing the acquired ECG data) representative of a quality of the placement of the device leads 120 on the subject 115. In particular, the requesting step can include generating a graphic prompt to the user 218 via the input 150 and output 155 to receive a user input score (e.g., "User Input Quality Score" or "User Score" on scale of 1 to 10) received from the user 218 for quality of placement of the device leads 120 based on the visual display of the acquired ECG data at the output 155.

Step 230 can also include applying the measure of the noise content to an algorithm in calculating an overall score of the quality of placement of the leads on the subject 115. The algorithm can further include a variable for the value of the "User Input Quality Score" or "User Score" received from the user 218 in response to the prompt described above, such that:

Overall Quality Score $(Q)=(A)*$Amount Noise Content/Amount of ECG data$+(B)*$User Input Quality Score Or Overall Quality Score $(Q)=(A)*$(Amount of ECG data−Amount of Noise Content)/Amount of ECG data$+(B)*$User Input Quality Score where variables (A) and (B) can be empirical weights applied to the algorithm either predetermined by the manufacturer or received from the user 218 of the quality control system 100.

A measure of the amount of noise content and the amount of ECG data can be in amount of bytes of data, or time period of one-hundred noise content and time period of ECG data. The step 230 can include the quality control system 100 automatically calculating the noise content and/or the overall quality score in response to receiving the input values for the variables of the algorithm of the overall score. Alternatively, the overall quality score can simply be a correlation of the time period of noise content described in step to a scale (e.g., 1 to 10).

Step 230 can include applying the quality score generated in step 225 to a rules engine represented by computer readable program instructions in the memory 140 for execution by the processor 145 to determine if any and which of a plurality of training modules to be completed by the hookup personnel 128. Step 230 can include comparing the overall quality score (Q) to a predetermined threshold to evaluate automatic triggering of a training request for the clinician associated with placement clinician that placed the device leads 120 in the acquisition of the subject ECG data.

If the overall score exceeds the threshold, step 235 can include automatically generating a request for the hookup personnel 128 to complete one or more selected training modules for proper placement of device leads 120 in acquisition of ECG data. The request can be in the form of an electronic message (e.g., email, text, phone message, etc.) to the placement clinician. Step 235 can include automatically searching and identifying one training module from a library or plurality of different training modules 240 for communication to the placement clinician based on the quality score generated in step 230. The training modules can include presentation slides, videos, audio snippets, etc. or combination thereof operable to educate the hookup personnel 128 in the proper protocol for placement of device leads 120 on the subject 115. The quality control system 100 can automatically select one training module from the library of modules 240 based on the overall score calculated in the steps described above. Step 245 can include automatically communicating the assignment or request for the hookup personnel or placement technician or hookup tech 128 to complete training of the selected one or more training modules in the library of modules 240.

Figure 3:
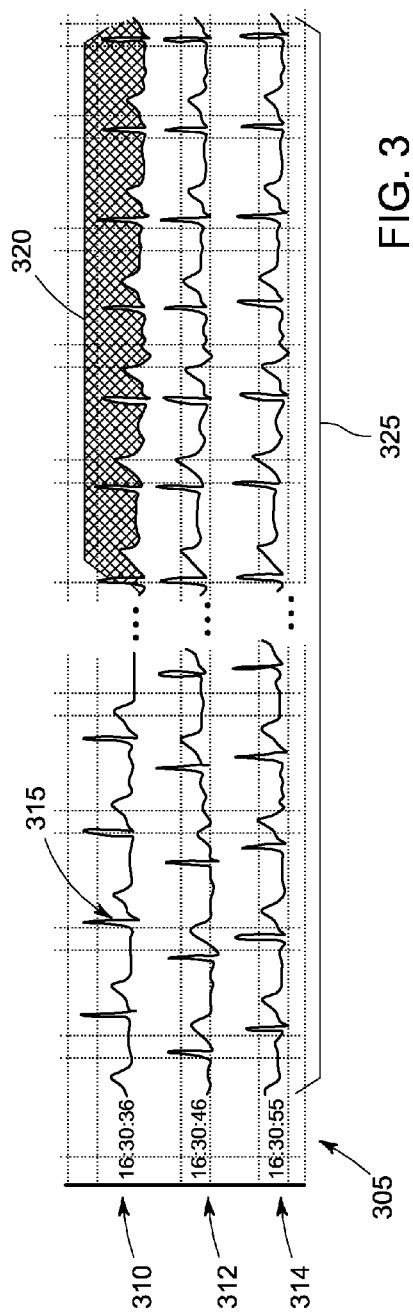
FIG. 3 shows a schematic diagram of an embodiment of a first display generated with the system and method in accordance to the subject matter described herein.

FIG. 3 shows a schematic diagram of an embodiment of a display 305 of the analysis for the noise content over a total duration time of three sets or case studies 310, 312, 314 of acquired device ECG data 315, acquired for three device leads 120 (see FIG. 1). The region 320 of the acquired device ECG data calculated or designated to be noise content can be visually illustrated with graphic cross-hatch lines or other visual graphic (e.g., color, frame, etc.) for illustration at the output 155. The measured value of the noise content can be equated in a measured time period of the noise content multiplied by the number of device leads (i.e., 8 hours×1 lead=8 lead-hours) placed by the hookup personnel 128 in acquisition of the device ECG data under analysis, and the total duration of device ECG data can be equated to a time period or duration 325 of acquired device ECG data under analysis by a number of leads placed by the hookup personnel 128 in the acquisition of the device ECG data (i.e., total duration=24 hours×3 leads=72 lead hours).

Figure 4:
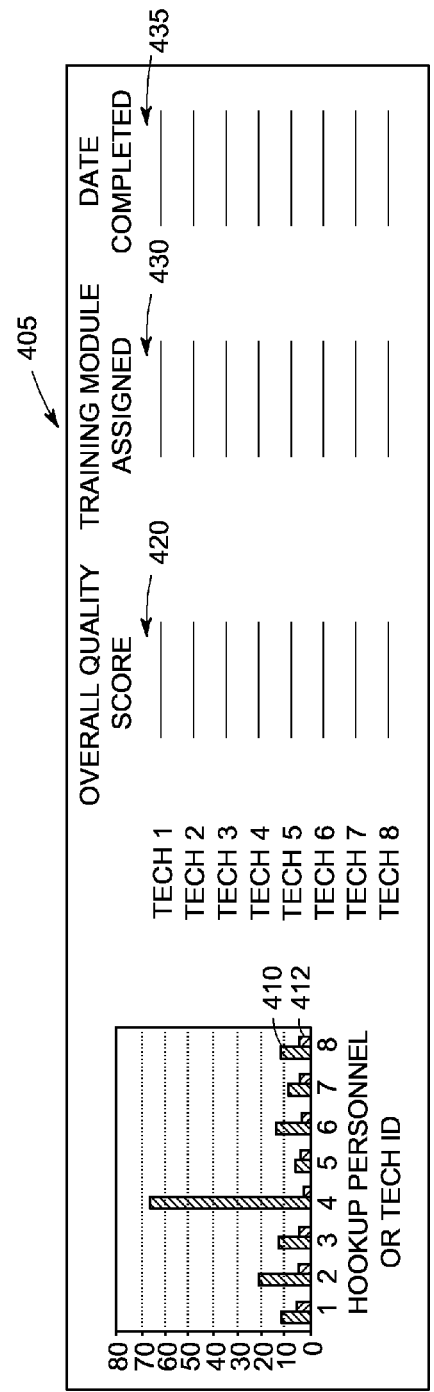
FIG. 4 illustrates a schematic diagram of an embodiment of another display generated by the system and method in accordance to the subject matter described herein.

FIG. 4 shows a schematic diagram of an embodiment of a display 405 for illustration at the output 155. The display 405 can include graphic illustrations (e.g., bar graph) 410, 412 that illustrates a measure of percentage noise content in the acquired device ECG data and the User Score or a user input quality score for each of a plurality of hookup personnel 128, respectively. The display 405 can further include a graphic illustration (e.g., numeric value) 420 of an overall quality score for each of the hookup personnel 128, as described above. The display 405 can further include other graphic illustrations, including the user input quality score versus hookup personnel 128, noise content versus device serial number, noise content versus device cable support serial number, noise content versus device lead, noise content removed versus hookup personnel 128 identification or user 218 identification, noise content versus time for each hookup personnel 128, average analysis time versus user 218 identification, completed quality analyses performed versus user 218 identification, requests 430 for device placement training modules to be completed for each hookup personnel 128 including a type of device placement training modules to be completed, date of completion 435 of device training modules, etc.

Figure 5:
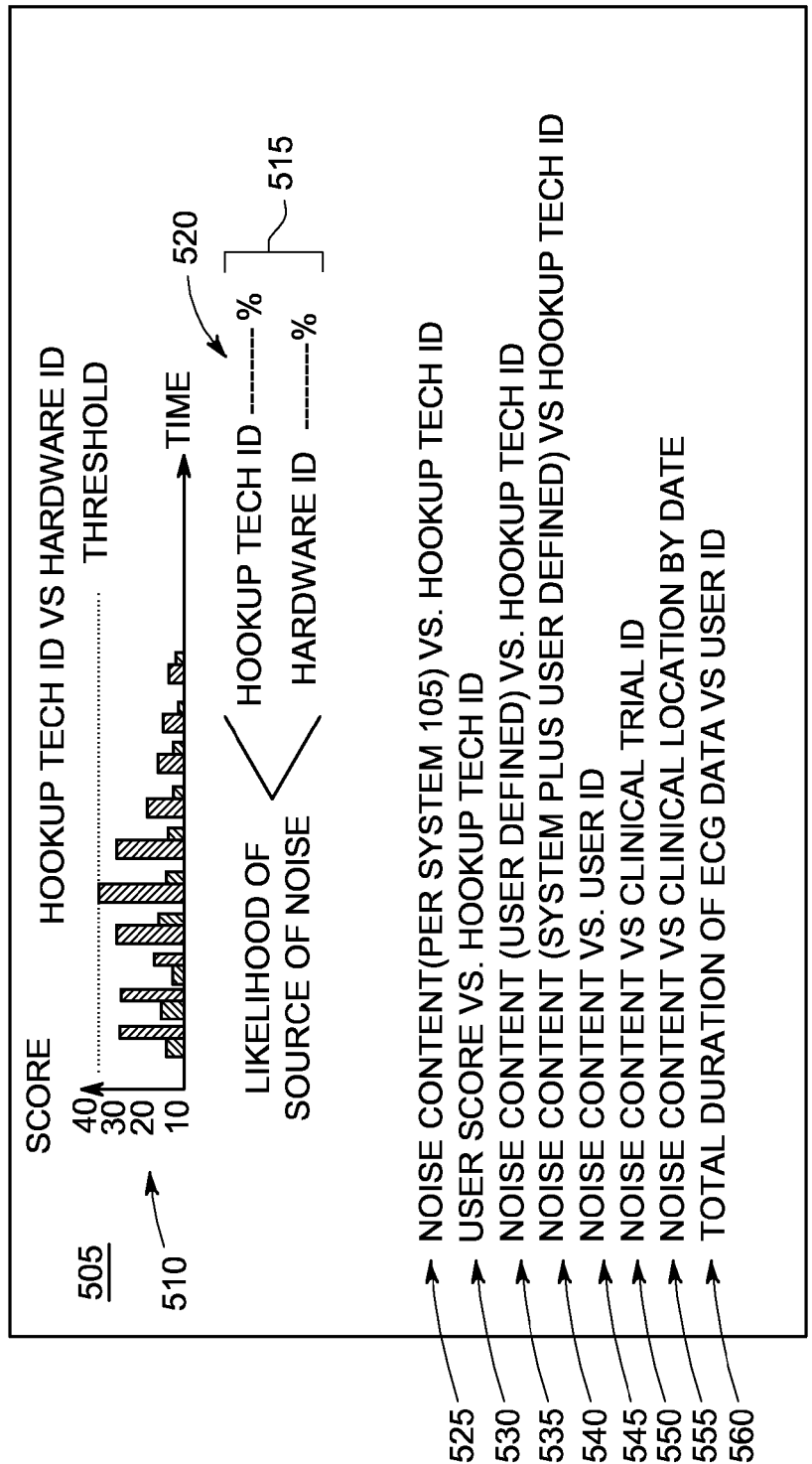
FIG. 5 illustrates a schematic diagram of an embodiment of another display generated by the system and method in accordance to the subject matter described herein.

FIG. 5 shows an embodiment of another display 505 generated by the quality control system 100 and method in accordance to the subject matter described herein. The display 505 can include a graphic illustration 510 of a change or trend in score of the hookup personnel 128 having a unique identifier (ID) or group over time relative to a trend in score a hardware (e.g., unique identifier (ID) of recording device, cable, lead, etc. or group thereof) over time. The display 505 can further include a graphic display 515 of a likelihood or a probability of the source of noise in the acquired ECG data is due to the hookup personnel ID versus the hardware ID used by the hookup personnel 128 in acquisition of the ECG data, the likelihood or probability calculated based on the trend in scores. The graphic display 515 of the likelihood can include a graphic illustration 520 of a percentage probability, or a color or graphic highlight of one of the unique identifier of the hookup personnel 128 or the unique identifier of the hardware have the increased likelihood of being the source of noise relative to the other. Based on this display 505, a user 218 can identify whether training of the hookup personnel 128 or replacement/maintenance of the hardware will most likely or have the greatest probability to reduce the noise attenuation in future acquisition of ECG data by the hookup personnel 128 or hardware. Similar the graphic illustration 510, the display 505 can further include a graphic illustration 525 of a trend in noise content (as identified by the ECG data analysis system 105) versus (vs.) the hookup personnel ID, a graphic illustration 530 of a trend in user quality score (as received from the user 218) vs. hookup personnel ID, graphic illustration 535 of a trend in noise content (as received from the user 218) vs. hookup personnel ID, a graphic illustration 540 of a trend in noise content (as calculated by ECG data analysis system 105 plus per instructions from the user 218) vs. hookup personnel ID, graphic illustration 545 of noise content vs. user ID, graphic illustration 550 of noise content vs. a clinical trial ID, graphic illustration 555 of noise content vs. clinic location with or without by date, and a graphic illustration 560 of total duration of ECG analysis time per each case study vs. user ID. The above-described graphic illustrations 510 through 560 can be illustrated as trends over time or per unique case studies in combination for comparison with one or more other graphic illustrations 510 (similar to graphic illustration 510) on the display 505 per user instructions or preprogrammed to the quality control system 100.

Technical effects of the above-described embodiments of the quality control system 100 and method 200 can include providing a display of a trend of noise content and/or quality score associated with the hookup personnel 128 and/or the hardware employed in the acquisition of ECG data over time. Another technical effect of the quality control system 100 and method 200 can include providing a likelihood or probability that the hookup personnel versus the hardware is the source of the noise content in the ECG data, based on the trend of noise content or quality score. If the quality control system 100 indicates that the hookup personnel 128 has the increased probability of being the source of the noise content, then the quality control system 100 can automatically assign training to be completed by the hookup personnel 128 directed to proper protocol in employing hardware in the acquisition of ECG data. If the quality control system 100 calculates that the hardware has the increased probability of being the source of the noise content, then the quality control system 100 can alert the user 218 of the need to replace or provide maintenance to the hardware.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

We claim:

1. A quality control system in combination with an ECG data analysis system to analyze ECG data acquired by a hardware that includes an ambulatory electrocardiography device via a cable having a plurality of leads connected to a subject, comprising:
   a non-transitory medium having a plurality of programmable instructions for execution by a processor to perform the steps of:
      calculating a trend of a quality score in the ECG data acquired from the subject dependent on a noise content in the ECG data; and
      calculating a probability that one of a hardware and the Hookup personnel, each associated with collecting the ECG data from the subject, is a substantial cause of the quality score for the ECG data, wherein the probability is calculated based on a comparison the trend of the quality score associated with the Hookup personnel versus the trend of the quality score of the hardware employed in acquiring the ECG data.

2. The quality control system of claim 1, wherein the quality score equals a percentage noise content in the acquired ECU data associated with one of:
   a unique identifier of the Hookup personnel that connected the ambulatory electrocardiography device to the subject, a unique identifier of the ambulatory electrocardiography device connected to the subject, a unique identifier of one of the plurality of leads connected to the subject, and the cable connecting the plurality of leads to the ambulatory electrocardiography device.

3. The quality control system of claim 2, wherein the hardware is one of the plurality of leads, the ambulatory electrocardiography device, and the cable connecting the plurality of leads to the ambulatory electrocardiography device employed in collected the ECG data from the subject.

4. The quality control system of claim 1 wherein the quality control system can calculate and create for display a quantification of the noise content in the ECG data acquired via each of the plurality of leads connected to the subject.

5. The quality control system of claim 4, wherein the quality control system further includes a library having a plurality of unique training modules directed to training in collecting of ECG data with the ambulatory electrocardiography device, and wherein in response to the probability that the source of noise is increased for the Hookup personnel relative to the hardware, the quality control system communicates an assignment to the Hookup personnel to complete one of the plurality of training modules in the library.

6. The quality control system of claim 1, wherein the quality score calculated by the quality control system includes a user quality score received from a user directed to one of the unique identifier of the Hookup personnel, a unique identifier of the ambulatory electrocardiography device, a unique identifier of one of the plurality of leads, and a unique identifier of a cable connecting the plurality of leads to the ambulatory electrocardiography device.

7. The quality control system of claim 6, wherein the quality control system automatically assigns one of a plurality of training modules over a remainder of the plurality of training modules based on one of the noise content calculated by the quality control system and the quality score calculated the quality control system.

8. The quality control system of claim 6, wherein the ECG data analysis system receives the ECG data via one of wireless or Bluetooth communication medium.

9. The quality control system of claim 1, wherein in response to the probability that the source of noise is increased for the Hookup personnel relative to the hardware, the quality control system communicates an assignment to the Hookup personnel to complete a training directed to proper protocol in collecting of ECG data with the ambulatory electrocardiography device.

10. A quality control system in combination with an ECG data analysis system to analyze ECG data acquired by a hardware that includes an ambulatory electrocardiography device via a cable having a plurality of leads connected to a subject, the improvement comprising: the quality control system creates a display of a probability that a unique hookup personnel versus the hardware is a source of noise detected in an acquired ECG data of the subject.

11. The quality control system of claim 10 wherein the ECG data acquisition includes a memory having a plurality of programmable instructions for execution by a processor to perform the steps of:

calculating a trend of a quality score in the ECG data associated with the Hookup personnel that connected the ambulatory electrocardiography device to the subject; and calculating a trend of a quality score of the hardware associated with collecting the ECG data from the subject, wherein the probability is calculated based on a comparison the trend of the quality score associated with the Hookup personnel versus the trend of the quality score of the hardware, wherein the hardware is one of the plurality of leads, the ambulatory electrocardiography device, or the cable connecting the plurality of leads to the ambulatory electrocardiography device.

12. The quality control system of claim 11, wherein the quality control system calculates and creates for display a quantification of the noise content in the ECG data acquired via each of the plurality of leads connected to the subject.

13. The quality control system of claim 11, wherein the quality score calculated by the quality control system includes a user quality score received from a user directed to one of the unique identifier of the Hookup personnel, a unique identifier of the ambulatory electrocardiography device, a unique identifier of one of the plurality of leads, and a unique identifier of a cable connecting the plurality of leads to the ambulatory electrocardiography device.

14. The quality control system of claim 11, wherein in response to the probability that the source of noise is increased for the Hookup personnel relative to the hardware, the quality control system communicates an assignment to the Hookup personnel to complete a training directed to proper protocol in collecting of ECG data with the ambulatory electrocardiography device.

15. The quality control system of claim 11, wherein the quality control system further includes a library having a plurality of unique training modules directed to training in collecting of ECG data with a r ambulatory electrocardiography device, and wherein in response to the probability that the source of noise is increased for the Hookup personnel relative to the hardware, the quality control system communicates an assignment to the Hookup personnel to complete one of the plurality of training modules in the library.

16. The quality control system of claim 11, wherein the quality control system further includes a library having a plurality of unique training modules directed to training in collecting of ECG data with an ambulatory electrocardiography device, and wherein in response to the probability that the source of noise is increased for the Hookup personnel relative to the hardware, the system communicates an assignment to the Hookup personnel to complete one of the plurality of training modules in the library.

17. The quality control system of claim 11, wherein the quality control system receives the ECG data via one of wireless or Bluetooth communication medium.

18. The quality control system of claim 11, wherein the quality control system quantifies the noise content by passing the ECG data through a band pass filter and designating the duration of time as noise content where a remainder of the ECG data falls below a minimum threshold.

19. The quality control system of claim 10, wherein the hardware is one of the plurality of leads, the ambulatory electrocardiography device, and the cable connecting the plurality of leads to the ambulatory electrocardiography device employed in collected the ECG data from the subject.

* * * * *